US00PP26260P2

(12) United States Plant Patent
Pieters et al.

(10) Patent No.: US PP26,260 P2
(45) Date of Patent: Dec. 22, 2015

(54) ***GUZMANIA* PLANT NAMED 'RED SKY'**

(50) Latin Name: *Guzmania hybrida*
Varietal Denomination: Red Sky

(71) Applicants: Luc Pieters, Laarne (BE); Caroline De Meyer, Laarne (BE)

(72) Inventors: Luc Pieters, Laarne (BE); Caroline De Meyer, Laarne (BE)

( * ) Notice: Subject to any disclaimer, the term of this patent is extended or adjusted under 35 U.S.C. 154(b) by 208 days.

(21) Appl. No.: 13/998,556

(22) Filed: Nov. 8, 2013

(51) Int. Cl.
*A01H 5/02* (2006.01)

(52) U.S. Cl.
USPC ..... Plt./371

(58) Field of Classification Search
USPC ..... Plt./371
See application file for complete search history.

*Primary Examiner* — Anne Grunberg
(74) *Attorney, Agent, or Firm* — C. A. Whealy

(57) ABSTRACT

A new and distinct cultivar of *Guzmania* plant named 'Red Sky', characterized by its upright and outwardly arching growth habit; dark green-colored leaves; large inflorescences with outwardly arching red-colored bracts; and good postproduction longevity.

2 Drawing Sheets

Botanical designation: *Guzmania hybrida.*
Cultivar denomination: 'RED SKY'.

BACKGROUND OF THE INVENTION

The present invention relates to a new and distinct cultivar of *Guzmania* plant, botanically known as *Guzmania hybrida* and hereinafter referred to by the name 'Red Sky'.

The new *Guzmania* plant is a product of a planned breeding program conducted by the Inventors in Laarne, Belgium. The objective of the breeding program is to create new *Guzmania* plants having unique bract colors and enhanced postproduction longevity.

The new *Guzmania* is a naturally-occurring whole plant mutation of *Guzmania hybrida* 'Indian Night', not patented. The new *Guzmania* plant was discovered and selected by the Inventors as a single flowering plant within a population of plants of 'Indian Night' in a controlled greenhouse environment in Laarne, Belgium in February, 2007.

Asexual reproduction of the new *Guzmania* plant by tissue culture in a controlled environment in Laarne, Belgium since April, 2007 has shown that the unique features of this new *Guzmania* plant are stable and reproduced true to type in successive generations.

SUMMARY OF THE INVENTION

Plants of the new *Guzmania* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Red Sky'. These characteristics in combination distinguish 'Red Sky' as a new and distinct *Guzmania* plant:

1. Upright and outwardly arching growth habit.
2. Dark green-colored leaves.
3. Large inflorescences with outwardly arching red-colored bracts.
4. Good postproduction longevity.

Plants of the new *Guzmania* can be compared to plants of the parent, 'Indian Night'. Plants of the new *Guzmania* differ primarily from plants of 'Indian Night' in bract color as plants of 'Indian Night' have purple-colored bracts.

Plants of the new *Guzmania* can be compared to plants of *Guzmania hybrida* 'Cherry', not patented. In side-by-side comparisons conducted in Laarne, Belgium, plants of the new *Guzmania* and 'Cherry' differed in the following characteristics:

1. Plants of the new *Guzmania* were more compact than plants of 'Cherry'.
2. Plants of the new *Guzmania* had shorter leaves than plants of 'Cherry'.
3. Plants of the new *Guzmania* and 'Cherry' differed in bract color as plants of 'Cherry' had orange red-colored bracts.
4. Bracts of plants of the new *Guzmania* were curved whereas bracts of plants of 'Cherry' were straight and not curved.

BRIEF DESCRIPTION OF THE PHOTOGRAPHS

The accompanying colored photographs illustrate the overall appearance of the new *Guzmania* plant showing the colors as true as it is reasonably possible to obtain in colored reproductions of this type. Colors in the photographs may differ slightly from the color values cited in the detailed botanical description which accurately describe the colors of the new *Guzmania* plant.

The photograph on the first sheet comprises a side perspective view of a typical flowering plant of 'Red Sky' grown in a container.

The photograph on the second sheet is a close-up view of a typical inflorescence of 'Red Sky'.

DETAILED BOTANICAL DESCRIPTION

The aforementioned photographs and following observations, measurements and values describe plants grown during the late winter in 19-cm containers in a glass-covered greenhouse in Laarne, Belgium and under cultural practices typical of commercial *Guzmania* production. During the production of the plants, day temperatures ranged from 21° C. to 30° C., night temperatures ranged from 20° C. to 21° C. and maximum light levels were 18,000 lux. Plants were three years old when the photographs and description were taken. In the following description, color references are made to The Royal Horticultural Society Colour Chart, 2007 Edition, except where general terms of ordinary dictionary significance are used.

Botanical classification: *Guzmania hybrida* 'Red Sky'.

Parentage: Naturally-occurring whole plant mutation of *Guzmania hybrida* 'Indian Night', not patented.

Propagation:

*Type*.—By tissue culture.

*Root description*.—Thick, fleshy; creamy white in color.

*Rooting habit*.—Medium density.

Plant description:

*Plant and growth habit*.—Upright and outwardly arching plant habit; broad inverted triangle; basal rosette of outwardly curved strap-like leaves affixed in tight spiral ranks; terminal inflorescence on an upright scape emerging from the center of the basal rosette; moderately vigorous to vigorous growth habit.

*Plant height, soil surface to top of inflorescence*.—About 59.5 cm.

*Plant diameter or spread*.—About 90.5 cm.

Leaf description:

*Arrangement*.—Basal rosette, spiral phyllotaxis; leaves sessile.

*Quantity of leaves per plant*.—Plants typically produce about 19 leaves prior to inflorescence development.

*Shape*.—Ligulate.

*Apex*.—Acuminate to short apiculate.

*Margin*.—Entire.

*Length*.—About 50.4 cm.

*Width*.—About 4.7 cm.

*Length of sheath*.—About 9.7 cm.

*Width of sheath*.—About 9.4 cm.

*Aspect*.—Leaves curved outward over their length and arching downward towards the apex.

*Texture, upper and lower surfaces*.—Leathery, stiff; smooth, glabrous.

*Venation*.—Parallel.

*Color*.—Developing leaves, upper surface: Slightly darker than between N137A and 147A. Developing leaves, lower surface: Close to N137B. Fully expanded leaves, upper surface: Darker than between N137A and 147A; venation, darker than between N137A and 147A; sheathed area, close to 148B. Fully expanded leaves, lower surface: Close to N137B; venation, close to N137B; sheathed area, close to 146B to 146C.

Inflorescence description:

*Inflorescence form*.—Terminal inflorescences with showy bracts; inflorescences supported on erect and strong scapes.

*Inflorescence length*.—About 20.2 cm.

*Inflorescence width*.—About 22.7 cm.

*Fragrance*.—None detected.

*Inflorescence longevity*.—Inflorescences of the new *Guzmania* are long-lasting; bract coloration is maintained for about four to five months; inflorescences persistent.

*Natural flowering season*.—Plants of the new *Guzmania* flower naturally from the late winter into spring.

*Flowers*.—Appearance and quantity: Single small flowers with about eleven flowers developing per inflorescence. Diameter, flattened: About 2.1 cm. Depth (height): About 6.7 cm.

*Flower buds*.—Length: About 6.2 cm. Diameter, flattened: About 1.7 cm. Shape: Lanceolate. Color: Close to 47A to 47B; towards the base, close to 160B.

*Petals*.—Quantity per flower: Three. Length: About 5.5 cm. Width: About 5 mm. Shape: Narrowly lanceolate. Apex: Obtuse. Margin: Entire. Texture, upper and lower surfaces: Smooth, glabrous; luster, moderately glossy. Color, immature and mature, upper surface: Close to 9C to 9D. Color, immature and mature, lower surface: Close to 9C to 9D.

*Petaloids*.—Quantity per flower: About twelve, arranged spirally. Length: About 5.5 cm. Width: About 1.3 cm. Shape: Oblong. Apex: Obtuse. Margin: Entire. Texture, upper and lower surfaces: Smooth, glabrous; luster, moderately glossy. Color, immature, upper and lower surfaces: Close to 51B; towards the base and apex, close to 160D. Color, mature, upper and lower surfaces: Close to 47A to 47B; towards the base, close to N144A; apex, close to 160D.

*Sepals*.—Quantity per flower: Three. Length: About 3.6 cm. Width: About 4 mm. Shape: Lanceolate. Apex: Acute. Base: Cuneate. Color, immature, upper and lower surfaces: Close to between 155C and 156D. Color, mature, upper and lower surfaces: Close to between 155C and 156D.

*Reproductive organs*.—Stamens: Quantity per flower: Six. Filament length: About 1.7 cm. Filament color: Close to 10D. Anther length: About 5 mm. Anther shape: Lanceolate. Anther color: Close to 10C to 10D. Pollen: None observed. Pistils: Quantity per flower: One. Pistil length: About 3.8 cm. Style length: About 3.7 cm. Style color: Close to 150D. Stigma shape: Clavate, three-lobed. Stigma color: Close to 151A. Ovary color: Close to 150D.

*Seeds and fruits*.—Seed and fruit production has not been observed on plants of the new *Guzmania*.

*Scape*.—Length: About 44.2 cm. Diameter: About 1.2 cm. Strength: Strong. Aspect: Typically erect. Texture: Smooth, glabrous. Color: Close to 150B.

*Terminal bracts*.—Length: About 17.6 cm. Width: About 4.4 cm. Shape: Lanceolate or ligulate. Apex: Acute. Base: Sheathing the scape. Margins: Entire. Texture, upper and lower surfaces: Smooth, glabrous. Color: When developing and fully developed, upper surface: Close to 46B; apex, close to 147A and 200A. When developing and fully developed, lower surface: Close to 46B; apex, close to 147B and N186C.

*Scape bracts*.—Length: About 27.5 cm. Width: About 4.2 cm. Shape: Lanceolate or ligulate. Apex: Acute. Base: Sheathing the scape. Margins: Entire. Texture, upper and lower surfaces: Smooth, glabrous. Color: When developing and fully developed, upper surface: Darker than between N137A and 147A; towards the base, close to 183A; sheathed area, close to 146D. When developing and fully developed, lower surface: Between 143C and 144A; sheathed area, close to 146D.

Temperature tolerance: Plants of the new *Guzmania* have been observed to tolerate high temperatures about 40° C. and to be hardy to USDA Hardiness Zone 10.

Disease & pest resistance: Plants of the new *Guzmania* have not been observed to resistant to pathogens and pests common to *Guzmania* plants.

It is claimed:

1. A new and distinct *Guzmania* plant named 'Red Sky' as illustrated and described.

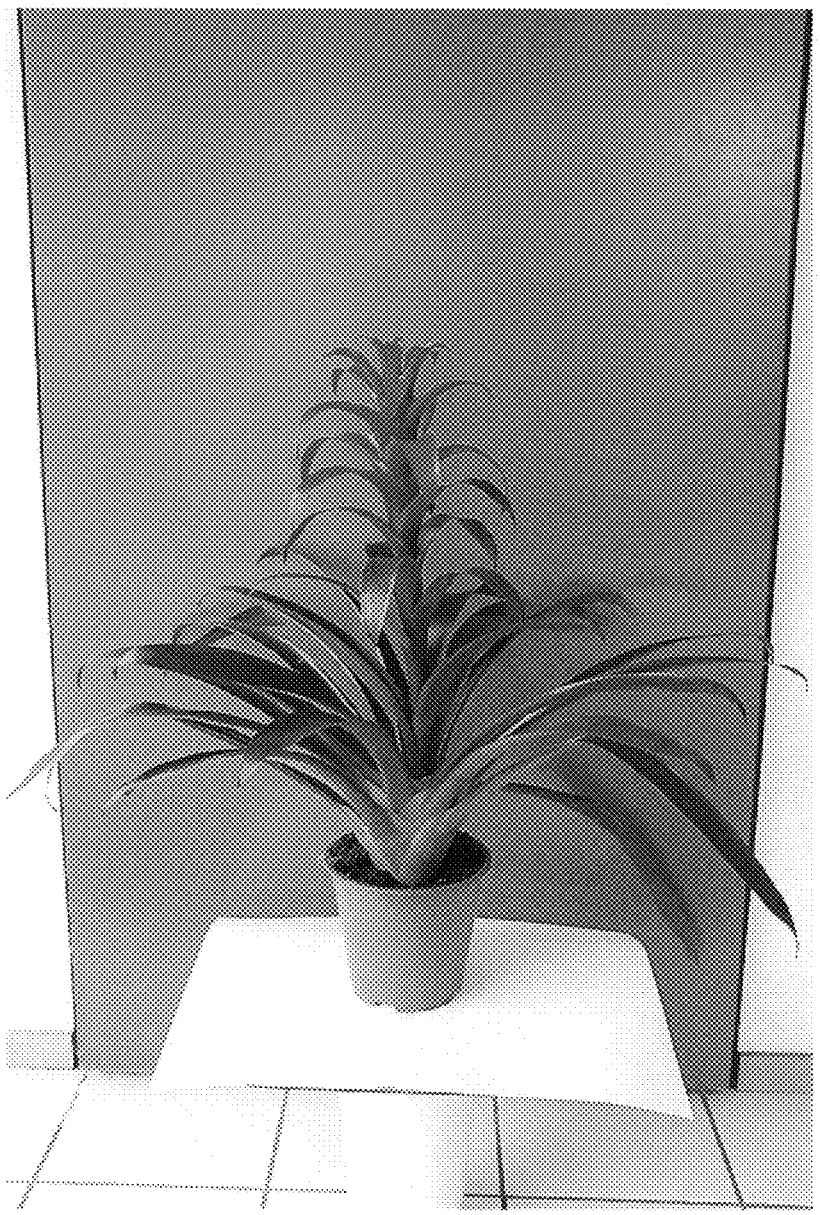

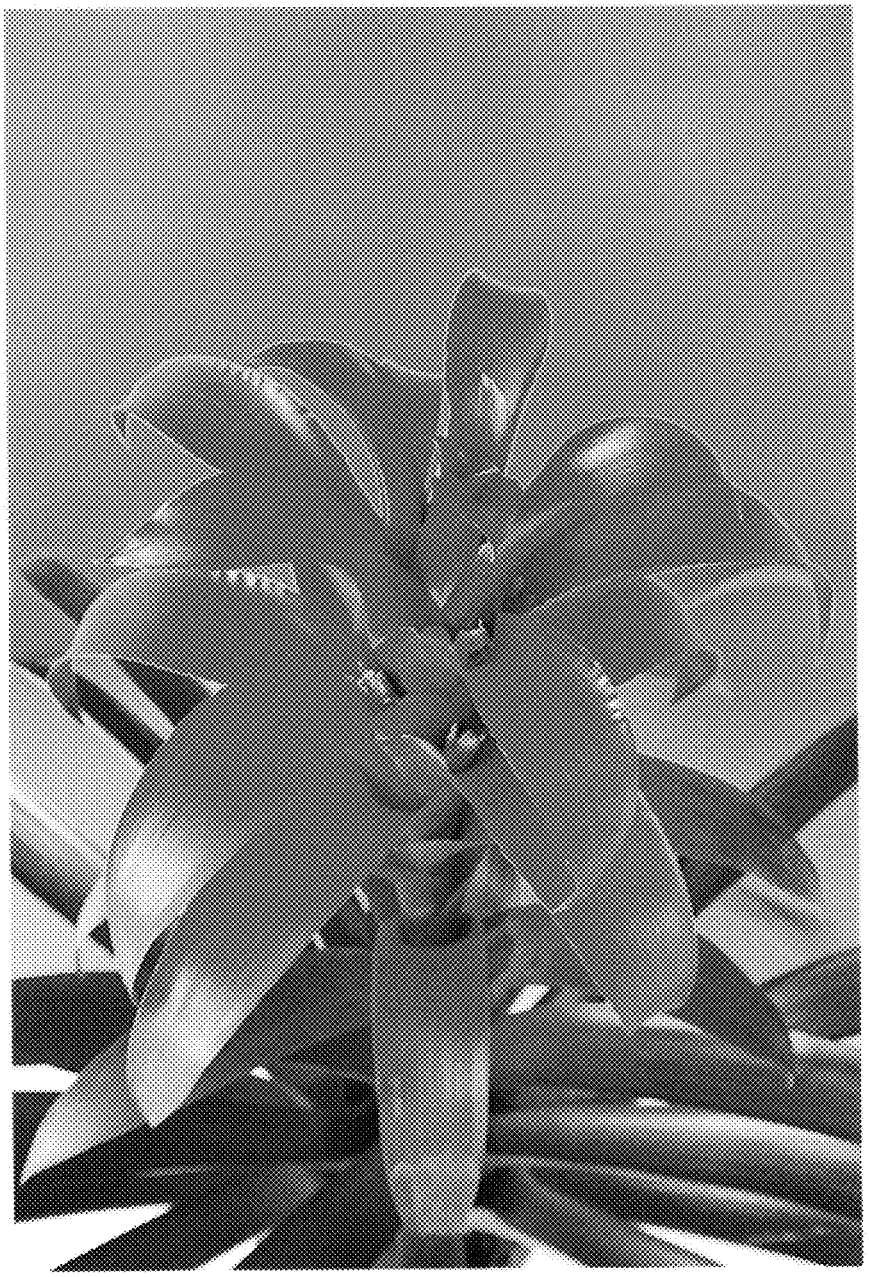

* * * * *